United States Patent
Tal et al.

(10) Patent No.: US 11,918,229 B2
(45) Date of Patent: *Mar. 5, 2024

(54) BLOOD FLOW REDUCER FOR CARDIOVASCULAR TREATMENT

(71) Applicant: Revamp Medical Ltd., Tel Aviv (IL)

(72) Inventors: Michael G. Tal, Savyon (IL); Lihu Avitov, Tel Aviv-Jaffa (IL); Raphael Benary, Tel Aviv (IL); Yael Shohat, Herzliya (IL)

(73) Assignee: Revamp Medical Ltd., Netania (IL)

( * ) Notice: Subject to any disclaimer, the term of this patent is extended or adjusted under 35 U.S.C. 154(b) by 282 days.

This patent is subject to a terminal disclaimer.

(21) Appl. No.: 16/525,389

(22) Filed: Jul. 29, 2019

(65) Prior Publication Data

US 2019/0343531 A1 Nov. 14, 2019

Related U.S. Application Data

(63) Continuation of application No. 15/717,607, filed on Sep. 27, 2017, now Pat. No. 10,363,044, which is a
(Continued)

(51) Int. Cl.
*A61B 17/00* (2006.01)
*A61B 17/12* (2006.01)
*A61B 90/00* (2016.01)

(52) U.S. Cl.
CPC .... *A61B 17/1215* (2013.01); *A61B 17/12022* (2013.01); *A61B 17/12036* (2013.01);
(Continued)

(58) Field of Classification Search
CPC .......... A61B 17/1215; A61B 17/12022; A61B 17/12036; A61B 17/1204;
(Continued)

(56) References Cited

U.S. PATENT DOCUMENTS

| 4,710,192 A | 12/1987 | Liotta et al. |
| 5,443,477 A | 8/1995 | Marin et al. |

(Continued)

FOREIGN PATENT DOCUMENTS

| EP | 2025360 A2 | 2/2009 |
| JP | 2004-533290 A | 11/2004 |

(Continued)

OTHER PUBLICATIONS

International Search Report issued in International Application No. PCT/IB2016/055763, date of mailing, Mar. 15, 2017.
(Continued)

*Primary Examiner* — Jing Rui Ou
(74) *Attorney, Agent, or Firm* — COOLEY LLP

(57) ABSTRACT

A blood flow reducing assembly includes a catheter shaft and an expandable occlusion member assembled with the catheter shaft. The expandable occlusion member includes foldable protrusions. One or more manipulation members are connected to the foldable protrusions and operative to move the foldable protrusions closer to or further away from one other. Movement of the foldable protrusions modifies occlusion ability of the foldable protrusions.

9 Claims, 8 Drawing Sheets

Related U.S. Application Data continuation of application No. PCT/IB2016/055763, filed on Sep. 27, 2016.

(60) Provisional application No. 62/252,599, filed on Nov. 9, 2015.

(52) U.S. Cl.
CPC .... *A61B 17/1204* (2013.01); *A61B 17/12109* (2013.01); *A61B 17/12136* (2013.01); *A61B 17/12145* (2013.01); *A61B 17/12168* (2013.01); *A61B 17/12177* (2013.01); *A61B 2017/00867* (2013.01); *A61B 2017/1205* (2013.01); *A61B 2090/0811* (2016.02); *A61B 2090/3966* (2016.02); *A61B 2090/3975* (2016.02)

(58) Field of Classification Search
CPC ........ A61B 17/12109; A61B 17/12136; A61B 17/12145; A61B 17/12168; A61B 17/12177; A61B 2017/00867; A61B 2017/1205; A61B 2090/0811; A61B 2090/3966; A61B 2090/3975
See application file for complete search history.

(56) References Cited

U.S. PATENT DOCUMENTS

| | | | |
|---|---|---|---|
| 5,683,451 A | 11/1997 | Lenker et al. | |
| 5,827,324 A | 10/1998 | Cassell et al. | |
| 6,638,293 B1 * | 10/2003 | Makower | A61B 1/3137 606/200 |
| 7,063,714 B2 | 6/2006 | Dorros et al. | |
| 7,935,075 B2 * | 5/2011 | Tockman | A61N 1/057 604/34 |
| 8,876,850 B1 | 11/2014 | Vollmers et al. | |
| 10,363,044 B2 | 7/2019 | Tal et al. | |
| 10,926,065 B2 | 2/2021 | Jönsson | |
| 2001/0002445 A1 * | 5/2001 | Vesely | A61F 2/2412 623/2.11 |
| 2002/0099407 A1 | 7/2002 | Backer et al. | |
| 2002/0115982 A1 | 8/2002 | Barbut et al. | |
| 2003/0023200 A1 | 1/2003 | Barbut et al. | |
| 2003/0153943 A1 | 8/2003 | Michael et al. | |
| 2003/0171771 A1 | 9/2003 | Anderson et al. | |
| 2004/0064090 A1 | 4/2004 | Keren et al. | |
| 2004/0243057 A1 | 12/2004 | Vinten-Johansen | |
| 2005/0055082 A1 * | 3/2005 | Ben Muvhar | A61F 2/848 623/1.15 |
| 2006/0064059 A1 | 3/2006 | Gelfand et al. | |
| 2006/0106449 A1 * | 5/2006 | Ben Muvhar | A61B 17/12172 623/1.15 |
| 2006/0106450 A1 | 5/2006 | Ben Muvhar | |
| 2007/0016286 A1 | 1/2007 | Herrmann et al. | |
| 2008/0058591 A1 | 3/2008 | Saadat et al. | |
| 2008/0183203 A1 | 7/2008 | Fitzgerald et al. | |
| 2010/0114022 A1 | 5/2010 | Hirszowicz et al. | |
| 2012/0059356 A1 | 3/2012 | Di Palma et al. | |
| 2014/0371778 A1 | 12/2014 | Rudakov et al. | |
| 2015/0005809 A1 | 1/2015 | Ayres et al. | |
| 2015/0032087 A1 | 1/2015 | Shibata et al. | |
| 2016/0375230 A1 * | 12/2016 | Lee | A61B 17/1204 604/509 |
| 2017/0049946 A1 | 2/2017 | Kapur et al. | |
| 2017/0100527 A1 | 4/2017 | Schwammenthal et al. | |
| 2017/0156840 A1 | 6/2017 | Edmiston et al. | |
| 2018/0014829 A1 | 1/2018 | Tal et al. | |
| 2021/0186517 A1 | 6/2021 | Tal et al. | |

FOREIGN PATENT DOCUMENTS

| | | |
|---|---|---|
| JP | 2010-522601 A | 7/2010 |
| JP | 2012502679 A | 2/2012 |
| JP | 2013017833 A | 1/2013 |
| WO | WO 2002/085443 A1 | 10/2002 |
| WO | WO 2014/201434 A2 | 12/2014 |
| WO | WO 2015/015314 A2 | 2/2015 |
| WO | WO 2017/031231 A1 | 2/2017 |
| WO | WO 2017/081561 A1 | 5/2017 |
| WO | WO-2017192912 A1 | 11/2017 |
| WO | WO-2018085890 A1 | 5/2018 |
| WO | WO 2018/197983 A1 | 11/2018 |

OTHER PUBLICATIONS

Extended European Search Report for Application No. EP20190896189, mailed on Oct. 31, 2022, 13 pages.

International Search Report and Written Opinion issued in PCT/IL2019/051360 date of mailing Apr. 7, 2020, 11 pages.

* cited by examiner

BLOOD FLOW REDUCER FOR CARDIOVASCULAR TREATMENT

RELATED APPLICATIONS

This application is a continuation of U.S. patent application Ser. No. 15/717,607, filed Sep. 27, 2017 (U.S. Pat. No. 10,363,044, issued Jul. 30, 2019), which is a continuation of PCT application no. PCT/IB2016/055763, filed Sep. 27, 2016, which claims the benefit of and priority to U.S. provisional application No. 62/252,599, filed Nov. 9, 2015. Each of the preceding is herein incorporated by reference in its entirety.

FIELD OF THE INVENTION

The present invention generally relates to apparatus and methods for altering blood flow or for altering or affecting preload and afterload in the cardiovascular system, such as to treat different conditions, such as but not limited to, venous hypertension or pulmonary edema in acute CHF (chronic heart failure) patients.

BACKGROUND OF THE INVENTION

Pulmonary edema, a medical emergency, is an accumulation of fluid in the lungs. Pulmonary edema is often caused by congestive heart failure. When the heart is not able to pump efficiently, blood can back up into the veins that take blood through the lungs.

As the pressure in these blood vessels increases, fluid is pushed into the air spaces (alveoli) in the lungs. This fluid reduces normal oxygen movement through the lungs. These two factors combine to cause shortness of breath.

Failure of the left side of the heart (left ventricle) causes blood to accumulate in the veins of the lungs (pulmonary veins), producing a dangerous rise in blood pressure within these veins. Sustained high pressure in the pulmonary veins eventually forces some fluid from the blood into the interstitial space and eventually to the surrounding microscopic air sacs (alveoli), which transfer oxygen to the bloodstream. As the alveoli fill with fluid, they can no longer provide adequate amounts of oxygen to the body.

Symptoms, especially severe breathing difficulty, develop over the course of a few hours and may be life-threatening. Although the outlook for pulmonary edema is favorable if the underlying disorder is treated in a timely fashion, the overall outcome for the patient depends upon the nature of the underlying disorder. Adults at high risk for heart failure are most commonly affected.

Typical treatment for patients presenting with pulmonary edema as a result of CHF is the administration of diuretic drugs, designed to reduce preload, which is described as the mechanical state of the heart at the end of diastole, the magnitude of the maximal (end-diastolic) ventricular volume or the end-diastolic pressure stretching the ventricles. In addition, vasodilation drugs are administered so as to reduce afterload—or the pressure against which the ventricle ejects blood.

SUMMARY OF THE INVENTION

The present invention seeks to provide apparatus and methods for altering or affecting blood flow or for altering or affecting preload and afterload in the cardiovascular system, such as to treat different conditions, such as but not limited to, pulmonary edema in acute CHF (chronic heart failure) patients or venous hypertension and other conditions.

In one embodiment, the blood flow reducing assembly includes a self-expandable element located at a distal end of an indwelling catheter. The self-expandable element has a distal end with a plurality of circumferentially placed, inwardly folding elements with hinge members, which allow the foldable elements to bend inwards (inwards radially). The hinge members permit the foldable elements to fold with minimal effect on the open diameter of the cylindrical section of the self-expandable elements.

The foldable elements (and in certain embodiments, some of the self-expandable elements) are coated or covered with a membrane or other covering, which is impervious to blood flow. The expandable distal end may be covered or coated while the foldable arms are in a semi-closed position so as to minimize excess material between the foldable arms as the reducer is being closed.

The degree of closure of the device (or the degree of inward folding of the foldable elements) is controlled by an operator using a handle located at the proximal end of the catheter. The handle may have an indicator showing the degree of closure of the reducer device.

The reducer may cause a Bernoulli Effect on the blood flow, with a jet flow exiting its central opening.

The reducer can be manipulated from an open to a fully or partially closed position.

There is provided in accordance with a non-limiting embodiment of the invention a blood flow reducing assembly including a catheter shaft, an expandable occlusion member assembled with the catheter shaft, the expandable occlusion member including loops, and manipulation members connected to the loops and operative to move the loops closer to or further away from one other, wherein movement of the loops modifies occlusion ability of the loops.

In accordance with an embodiment of the invention movement of the loops closer to one another increases occlusion ability of the loops and movement of the loops further from one another decreases occlusion ability of the loops.

In accordance with one non-limiting embodiment of the invention, the occlusion member includes interconnecting struts and the loops are connected to at least some of the struts by hinge members, which allow the loops to pivot with respect to the struts in one or more directions. The hinge members may be circumferentially distributed about distal ends of some or all of the struts. The loops may be extendable axially from the hinge members in a fully open position or are foldable inwards towards each other in a partially or fully closed position.

In accordance with an embodiment of the invention a covering at least partially covers the expandable occlusion member, the covering being impervious to blood flow.

In accordance with an embodiment of the invention the manipulation members include one or more connecting links connected to the loops, the connecting links extending to a handle located at a proximal end of the catheter shaft, wherein manipulation of the handle moves the loops to modify occlusion ability of the loops. When the loops are moved closer to one another, a space called an orifice is left open in the covering.

In accordance with an embodiment of the invention an indicator is on the handle configured to indicate a degree of closure of the loops.

In accordance with another non-limiting embodiment of the invention the catheter shaft includes a telescoping shaft that includes an inner shaft arranged to slide in an outer shaft, and the loops include helical loops positioned between proximal and distal ends of the occlusion member, the proximal end of the occlusion member being secured to one of the inner and outer shafts and the distal end of the occlusion member being secured to the other one of the inner and outer shafts, and wherein decreasing a distance between the proximal and distal ends causes the loops of the occlusion member to bunch together, and wherein the manipulation members are the inner and outer shafts.

In accordance with an embodiment of the invention the expandable occlusion member includes a balloon with a portion formed into the loops.

The expandable occlusion member may be self-expanding or fluidly expandable, for example.

BRIEF DESCRIPTION OF THE DRAWINGS

The present invention will be understood and appreciated more fully from the following detailed description, taken in conjunction with the drawings in which.

DETAILED DESCRIPTION OF EMBODIMENTS

Figure 1:
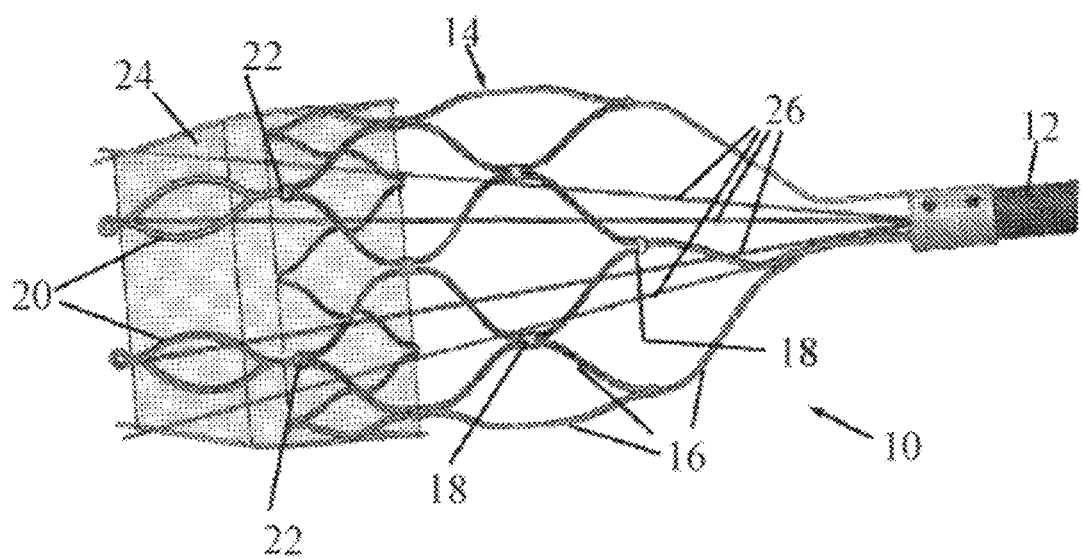
FIG. 1 is a simplified pictorial illustration of a blood flow reducing assembly, constructed and operative in accordance with a non-limiting embodiment of the invention.

Reference is now made to FIG. 1, which illustrates a blood flow reducing assembly 10, constructed and operative in accordance with a non-limiting embodiment of the invention.

Assembly 10 includes a shaft, such as a flexible catheter shaft 12, and an expandable occlusion member 14 assembled with shaft 12. The occlusion member 14 may be initially disposed in shaft 12 and deployed out of shaft 12 such as by pushing occlusion member 14 out of shaft 12. Alternatively, occlusion member 14 may be mounted at the distal end of shaft 12 (not inside shaft 12). The expandable occlusion member 14 may be self-expanding (e.g., constructed of a shape memory material, such as but not limited to, Nitinol) or expandable by mechanical means (e.g., wires that push/pull expandable elements) or expandable by fluid means (e.g., hydraulic or pneumatic inflation/deflation of flexible members, such as but not limited to, balloons).

The expandable occlusion member 14 may expand radially (and/or axially) and conform to the shape of the body lumen (e.g., blood vessel) in which it is deployed. The expandable occlusion member 14 may be generally cylindrical in shape (although other shapes are within the scope of the invention). The expanded size of occlusion member 14 may be greater than the internal perimeter of the body lumen, so that occlusion member 14 may be used to remodel the shape of the body lumen.

In this embodiment, the occlusion member 14 is constructed of interconnecting struts 16, such as wires or other slender elements, which may be bent or otherwise formed into loops that are interconnected at wire folds 18. This structure of interconnecting struts 16 can be easily compressed and subsequently expanded to a predetermined shape.

The expandable occlusion member 14 may include one or more foldable protrusion 20 (which may be formed as loops). The foldable protrusions 20 may be connected to at least some (or all) of the struts 16. In the illustrated embodiment, foldable protrusion 20 is connected to the distal end of the strut 16 by a hinge member 22, which allows the foldable protrusion 20 to pivot about the distal end of the strut 16 in one or more directions. Hinge members 22 are circumferentially distributed about the distal ends of some or all of the struts 16. The foldable protrusions 20 can extend axially from hinge members 22 in a fully open position or can fold inwards towards each other in a partially or fully closed position.

A covering 24 is provided at the distal end of assembly 10. Covering 24 may cover the foldable protrusions 20 and may also cover part of the distal ends of the struts 16 and part of the hinge members 22 or other parts of occlusion member 14. Covering 24 may be a membrane which is impervious to blood flow. One or more connecting links 26, such as wires or threads and the like, may be connected to (e.g., the distal end of) each of the foldable protrusions 20. The connecting links 26 extend through the axial length of the catheter shaft 12 to a handle 28 (FIG. 3) located at a proximal end of shaft 12. Handle 28 includes a control knob 30, which may be connected to an internal controllable spindle connected to connecting links 26. The control knob 30 can be used to pull or otherwise manipulate connecting links 26, thereby pulling the foldable protrusions 20 inwards in a radial direction, effectively creating a resistance to the flow in the body lumen. In other words, movement of the foldable protrusions 20 closer to one another creates or increases occlusion of the flow in the body lumen.

Figure 2A:
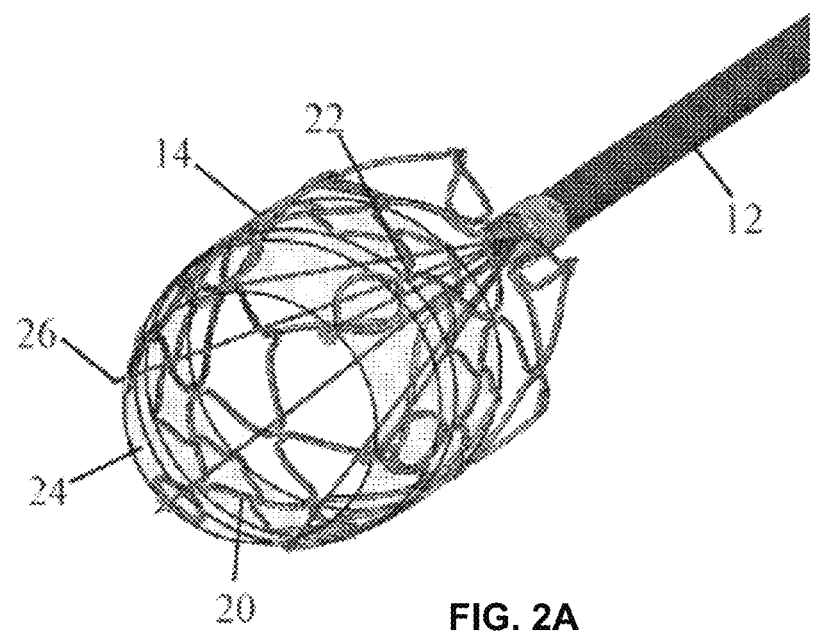
FIGS. 2A and 2B are simplified pictorial illustrations of the blood flow reducing assembly in full flow and restricted flow (e.g., closed or almost closed) positions, respectively.
Figure 2B:
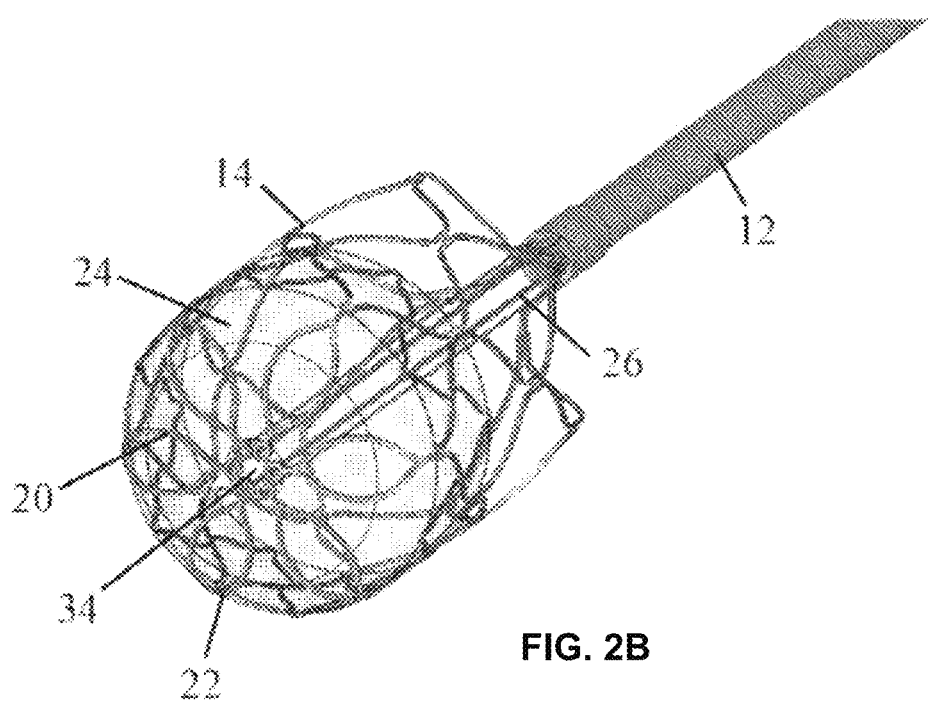
Figure 3:
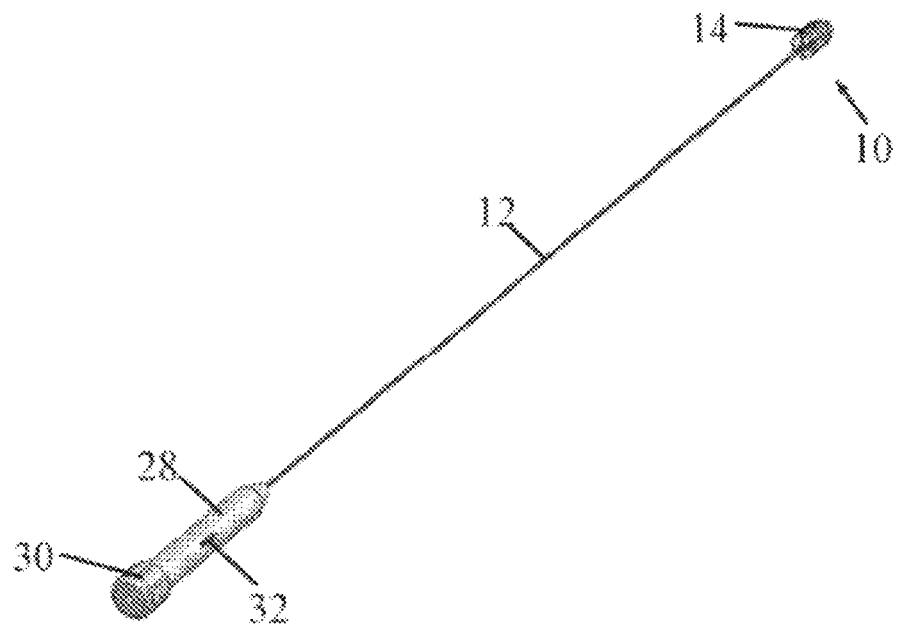
FIG. 3 is a simplified pictorial illustration of the blood flow reducing assembly mounted on a shaft connected to a manipulating handle, in accordance with a non-limiting embodiment of the invention.
Figure 4:
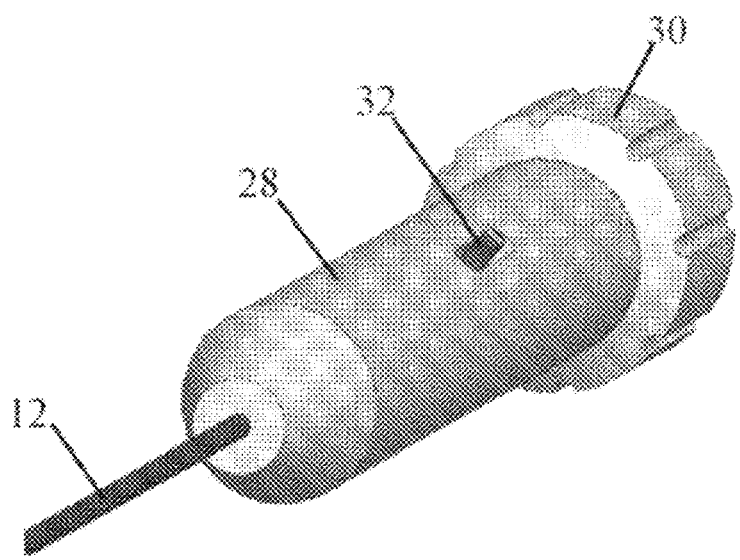
FIG. 4 is a simplified pictorial illustration of the manipulating handle, showing an indicator of the degree of closure.

FIG. 2A illustrates foldable protrusions 20 extended axially from hinge members 22 in a fully open position. The connecting links 26 have not been pulled inwards. FIG. 2B illustrates foldable protrusions 20 folded inwards towards each other in a partially or fully closed position. The connecting links 26 have been pulled inwards to fold the foldable protrusions 20 inwards towards each other. The connecting links 26 are manipulation members that modify the occlusion ability of foldable protrusions 20. The degree of closure can be controlled by handle 28 (control knob 30). As seen in FIGS. 3 and 4, an indicator 32 may be provided on handle 28 to indicate the degree of closure.

When the foldable protrusions 20 are brought to a closed (or inward position), flow downstream of the foldable protrusions 20 and occlusion member 14 is reduced. The blood flow exits the flow reducer by flowing through space left open in covering 24 (referred to as orifice 34—FIG. 2B), that is, through the center where the foldable protrusions 20 are not fully folded inwardly. The blood thus flows from a relatively large diameter of the distal elements 14 through the relatively small diameter of orifice 34 and then back to the body lumen, which has a large diameter than orifice 34. This creates a Venturi Effect (based on the Bernoulli Effect), in which the flow through orifice 34 has a lower pressure and higher velocity, which can be used to affect the pressure regime directly downstream of the blood flow reducing assembly 10.

Figure 5:
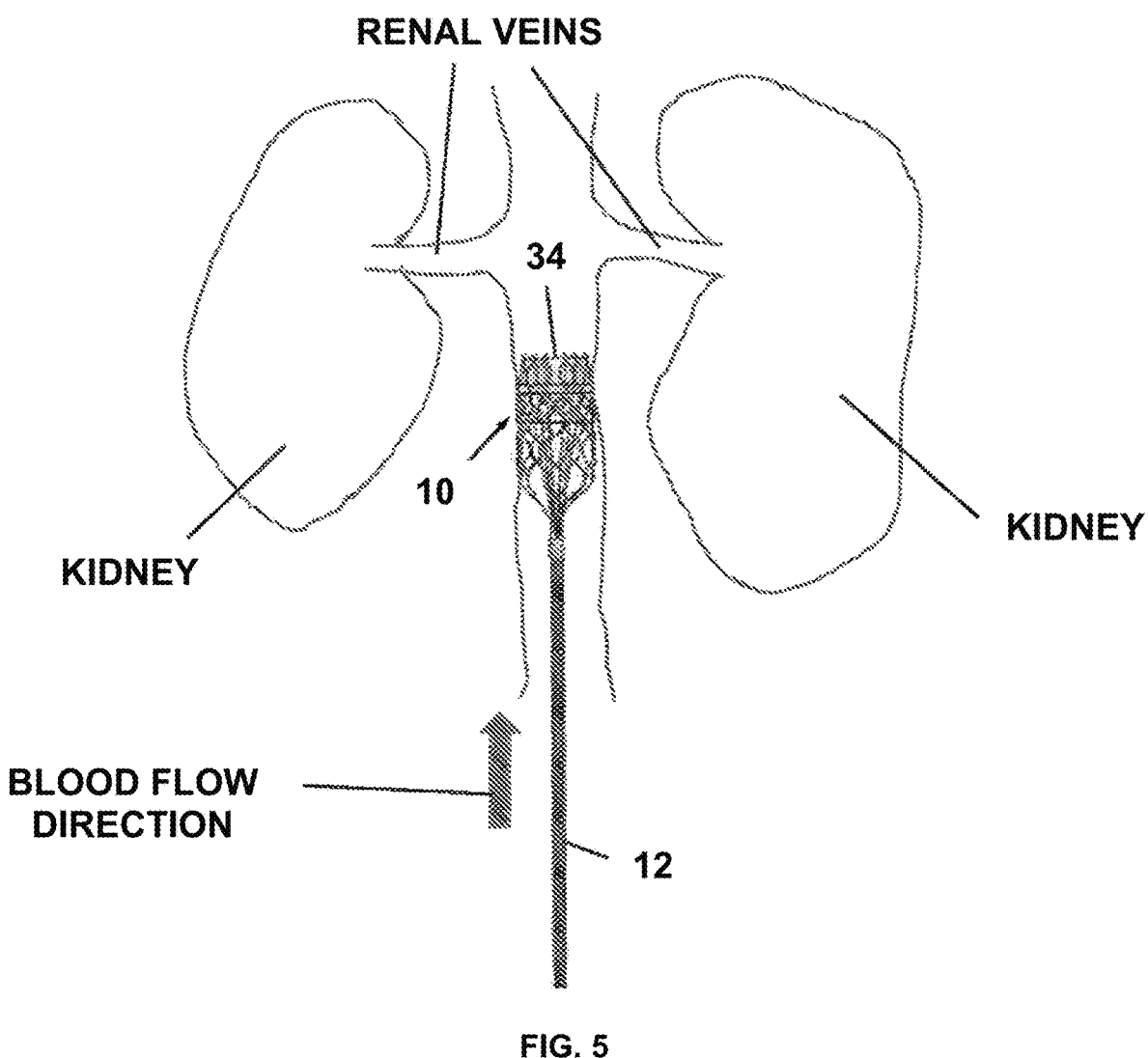
FIG. 5 is a simplified pictorial illustration of the blood flow reducing assembly mounted on the shaft and introduced into a body lumen, in accordance with a non-limiting embodiment of the invention.

Reference is now made to FIG. 5, which illustrates the blood flow reducing assembly 10 mounted on shaft 12 and introduced into a body lumen, in accordance with a non-limiting embodiment of the invention. The assembly is shown introduced into a blood vessel leading to the kidneys, upstream of the renal veins.

As described above, when assembly 10 is in its closed position, a jet flow of blood may flow through the orifice 34 generally towards the center of the inferior vena cava (IVC). Because of the Bernoulli Effect, a region near the center of the IVC is created which has increased blood velocity and reduced pressure, which draws blood from the renal veins (increasing pressure drop over the kidneys). The assembly 10 can pool blood in the lower extremities and reduce the flow of blood into the right atrium which reduces preload.

The flow restriction can thus be used to control the volume, pressure or venous capacitance of blood returning to the right atrium of the heart via the inferior vena cava and/or the superior vena cava, thereby to decrease venous return. By controlled obstruction of the IVC, SVC or both, it is surmised that blood may pool in the venous system, thus decreasing venous blood return to the right atrium and affecting preload.

Figure 6:
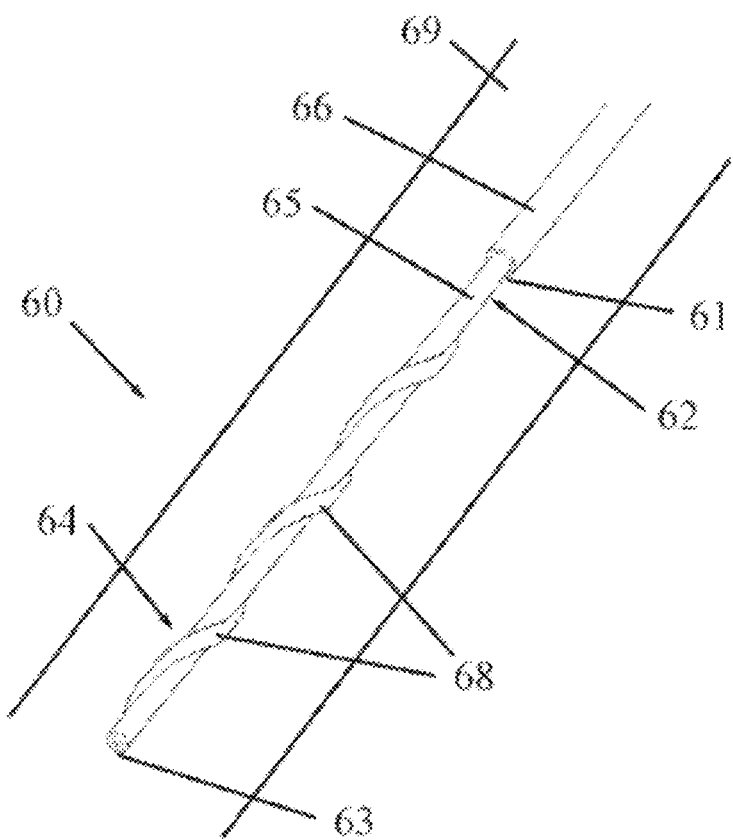
FIG. 6 is a simplified pictorial illustration of a blood flow reducing assembly, constructed and operative in accordance with another non-limiting embodiment of the invention.
Figure 7A:
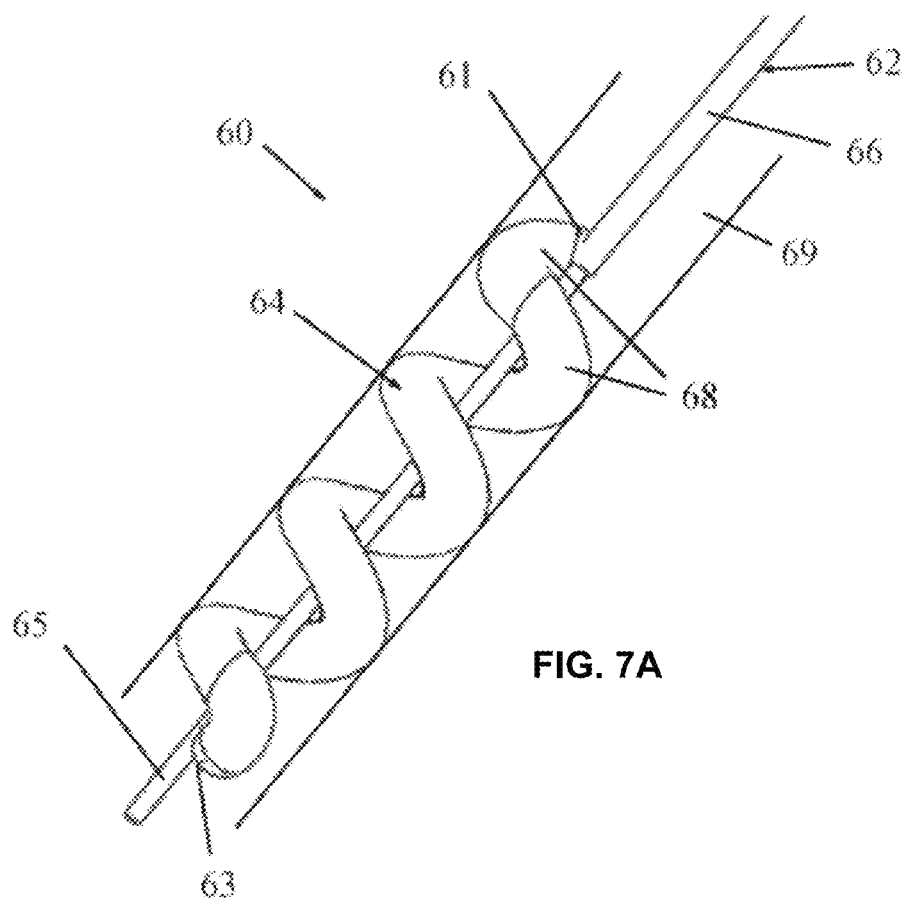
FIG. 7A is a simplified pictorial illustration of loops of the blood flow reducing assembly partially bunched together and partially expanded radially outwards to achieve partial occlusion.
Figure 7B:
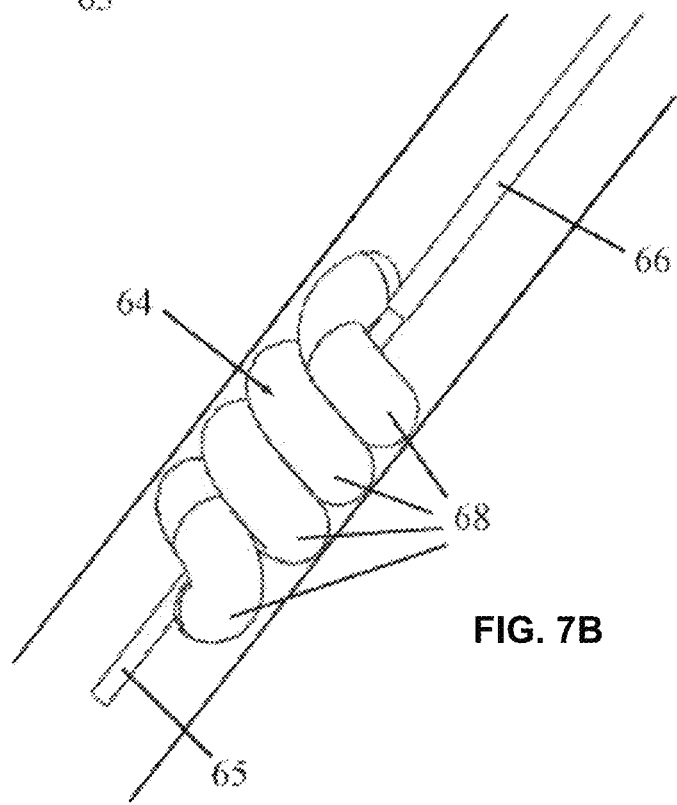
FIG. 7B is a simplified pictorial illustration of the loops fully bunched together and fully expanded radially outwards to reach maximum occlusion.

Reference is now made to FIGS. 6-7B, which illustrate a blood flow reducing assembly 60, constructed and operative in accordance with another non-limiting embodiment of the invention.

Assembly 60 includes a shaft, such as a flexible catheter shaft 62, and an expandable occlusion member 64 assembled with shaft 62. In the illustrated embodiment, catheter shaft 62 is a telescoping shaft that includes an inner shaft 65 arranged to slide in an outer shaft 66. The occlusion member 64 may be initially disposed in shaft 62 (such as being wrapped around a portion of inner shaft 65) and deployed out of shaft 62 such as by pushing occlusion member 64 out of shaft 62. Outer shaft 66 may be concentric with inner shaft 65.

In the illustrated embodiment, expandable occlusion member 64 is helical having multiple coils or loops 68 positioned between proximal and distal ends 61 and 63, respectively, of occlusion member 64. The proximal end 61 is secured to outer shaft 66 and the distal end 63 is secured to inner shaft 65 (alternatively, the opposite may be done). By suitable longitudinal axial movement of either inner shaft 65 or outer shaft 66, the distance between proximal end 61 and distal end 63 is either decreased or increased. Decreasing the distance between proximal end 61 and distal end 63 causes the loops 68 of occlusion member 64 to bunch together. FIG. 7A shows the loops 68 partially bunched together and partially expanded radially outwards thus achieving partial occlusion, and FIG. 7B shows the loops 68 fully bunched together and fully expanded radially outwards, thus reaching maximum occlusion. FIG. 6 shows the maximum distance between proximal end 61 and distal end 63, in which case the loops 68 of occlusion member 64 are snugly wrapped around inner shaft 65 and present minimum occlusion.

As in the previous embodiment, a control knob (not shown) can be used to manipulate the inner and outer shafts to expand or contract the loops 68 to increase or decrease resistance to the flow in a body lumen 69. Movement of the loops 68 closer to one another creates or increases occlusion of the flow in the body lumen 69. The inner and outer shafts 65 and 66 are manipulation members that modify the occlusion ability of loops 68.

In the illustrated embodiment, the expandable and helical occlusion member 64 is constructed of a balloon, a portion of which is wound into loops 68. The balloon may be hydraulically or pneumatically inflated and deflated, and as such, its stiffness can be controlled by the amount it is inflated. Alternatively, the expandable and helical occlusion member 64 may be self-expanding (e.g., constructed of a shape memory material, such as but not limited to, Nitinol).

The balloon may be introduced through body lumen 69 while in the deflated state and positioned using methods known in the art. Fiduciary markers, such as but not limited to radiopaque markers or optically sensed markers, may be placed on the device at selected areas to assist the placement of the device. Once in place, the spiral balloon is inflated, creating a helical flow occlusion member which can disrupt or occlude blood flow in the anterograde direction without completely occluding the vessel.

Figure 8:
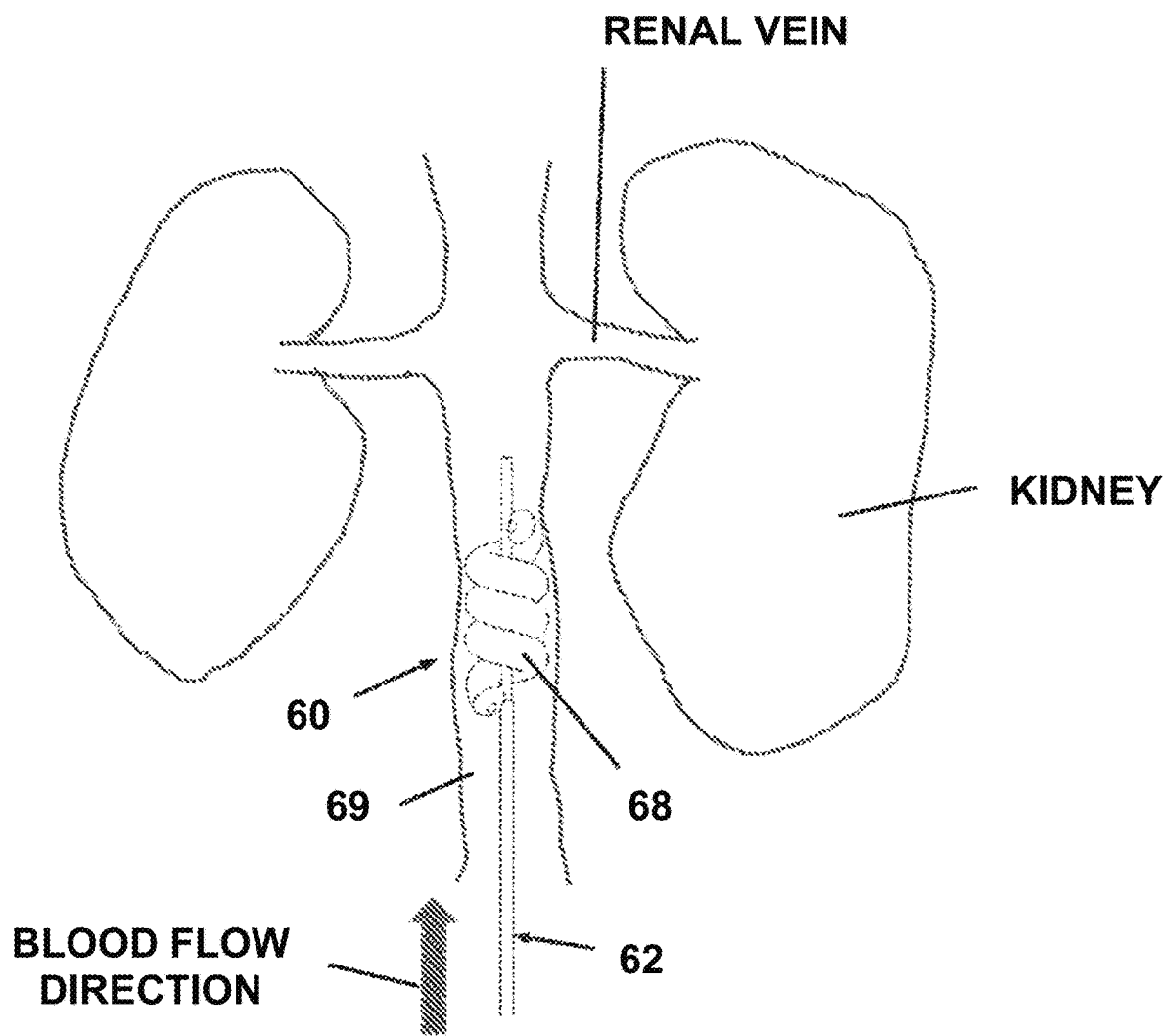
FIG. 8 is a simplified pictorial illustration of the blood flow reducing assembly of FIGS. 6-7B mounted on the shaft and introduced into a body lumen, in accordance with a non-limiting embodiment of the invention.

Reference is now made to FIG. 8, which illustrates the blood flow reducing assembly 60 introduced into body lumen 69, in accordance with a non-limiting embodiment of the invention. The assembly is shown introduced into a blood vessel leading to the kidneys, upstream of the renal veins.

Figure 9:
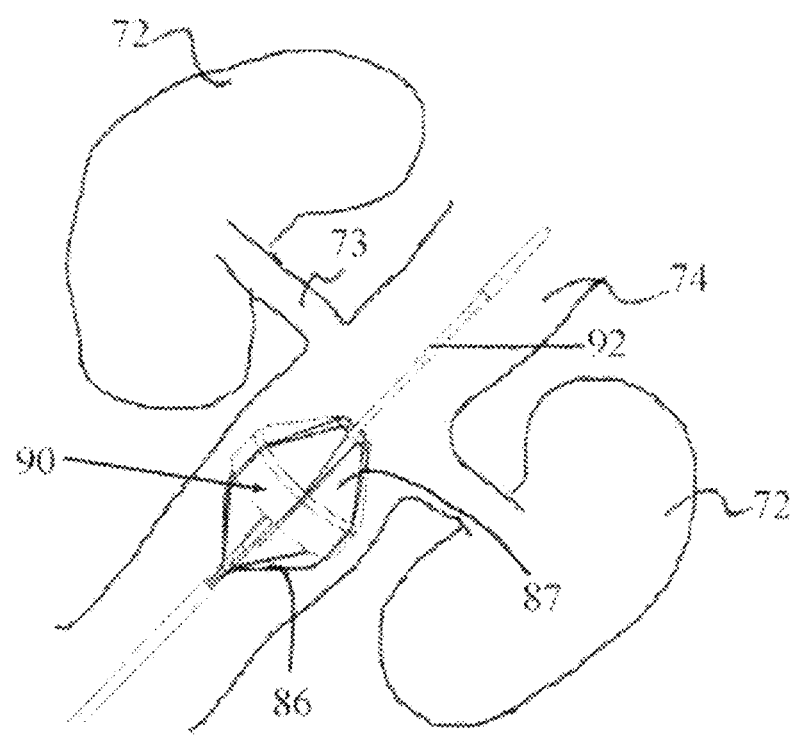
FIG. 9 is a simplified pictorial illustration of a blood flow reducing assembly, constructed and operative in accordance with another non-limiting embodiment of the invention.

Reference is now made to FIG. 9, which illustrates another blood flow reducing assembly of the invention in which an expandable occlusion member 90 is placed into a body lumen such as inferior vena cava 74. The expandable occlusion member 90 may be a conical element as shown, but it can also be a flat orifice. The expandable occlusion member 90 is placed near the inlet of the renal veins 73 thus creating an area of reduced pressure at the distal end of a conical member which has a distal end smaller in diameter than its proximal end. The area of lower pressure in the inlet area of the renal vein inlets increases the overall pressure gradient experienced by the kidneys 72.

In the embodiment of FIG. 9, the expandable occlusion member 90 is a truncated conical element, provided with proximal and distal ends 86 and 87, wherein the proximal end 86 is located upstream of the conical element relative to antegrade flow and the distal end 87 is located downstream of the conical element, and the proximal end of the conical element has a larger diameter than the distal end of the truncated conical element. The truncated conical element is located on an inner shaft of a delivery catheter 92 having one or more internal shafts, and one or more external shafts, whereby the external shaft can govern the radial expansion of the truncated conical section by the relative movement of the external shaft relative to the inner shafts of the delivery catheter (as described above for the embodiment of FIGS. 6-8). The proximal end of the truncated conical element may or may not come into contact with the tissue of the surrounding body lumen. The angles defined by the conical wall section to the central axis of the truncated conical element can vary, without limitation, from 90°—which would characterize a flat element with a critical orifice, to 5° which would make for an elongated conical element. The expandable occlusion member described may also take more complex forms other than straight truncated cones.

The blood entering the proximal end of the truncated conical element (expandable occlusion member) will gradually accelerate as it flows in the antegrade direction through the truncated conical element. The velocity of the fluid jet exiting the distal end of the conical element as it discharges back into the body lumen will be greater than the velocity of the fluid at the proximal end of the conical element and will therefore have a lower pressure than that at the proximal end of the device. The flow through the truncated conical element or through the orifice described above can be described by using Bernoulli's equation:

$$p_1 - p_2 = \frac{\rho}{2}(v_2^2 - v_1^2)$$

Where: P1 and P2 are the pressures before and at the constriction respectively, p is the density of blood, and V1 and V2 are the blood velocities before and at the constriction respectively.

Placement of this device in the inferior vena cava, caudal to the inlet of the renal veins, creates a lower pressure zone in the area, thereby increasing the pressure gradient on the kidneys and improving renal function.

What is claimed is:

1. An adjustable blood flow method for adjustably reducing blood flow within a blood vessel comprising:
    positioning an expandable element of an adjustable blood flow assembly within a blood vessel having a blood vessel diameter (BVD), the expandable element including:
        a cylindrical wire structure comprising a plurality of wire elements;
        a proximal end and a distal end;
        a cylindrical section having a first diameter, the first diameter corresponding at least approximately to the BVD;
        an adjustable, radially inwardly foldable outer circumference (IFOC) comprising a plurality of foldable protrusions forming the distal end; and
        a blood impervious cover configured to cover a surface of at least the IFOC such that the surface of the IFOC is integral;
    and
    adjusting the IFOC via a handle located outside of the blood vessel such that the IFOC forms a blood flow orifice at the distal end having a second diameter smaller than the first diameter so as to produce a desired reduced blood flow from the orifice,
    wherein:
        the IFOC is operably connected to one or more connecting links extending from the expandable element to the handle via a shaft,
        each foldable protrusion comprises a wire element extending from the cylindrical wire structure forming a loop;
        and
        the second diameter is established via pulling of the one or more connecting links in a direction toward the handle such that the IFOC folds inward.

2. The method of claim 1, wherein the expandable element includes:
    the proximal end is configured for placement in an upstream direction of a blood flow in the blood vessel;
    and
    the distal end is configured for placement in a downstream direction of the blood flow in the blood vessel.

3. The method of claim 2, wherein the IFOC is arranged on or near the distal end.

4. The method of claim 1, wherein the expandable element includes a plurality of interconnecting struts.

5. The method of claim 4, wherein a set of the struts forms the IFOC.

6. The method of claim 5, wherein the set of struts forming the IFOC is operably connected to the one or more connecting links.

7. The method of claim 6, wherein movement of the connecting links via the handle cause the set of struts of the IFOC to fold the IFOC inwardly so as to reduce the second diameter.

8. The method of claim 1, wherein:
    the IFOC includes a plurality of foldable protrusions pivotable inwardly relative to the longitudinal axis; and
    the assembly further includes the catheter shaft, wherein the expandable element is integral with or otherwise attached to a distal end of the shaft.

9. The method of claim 1, wherein the assembly further comprises the handle.

* * * * *